US00PP25632P3

(12) United States Plant Patent

Maillard et al.

(10) Patent No.: US PP25,632 P3

(45) Date of Patent: Jun. 23, 2015

(54) NECTARINE TREE NAMED 'CAKEDELICE'

(50) Latin Name: ***Prunus persica* var *nucipersica*.(L.) Batsch**
Varietal Denomination: CAKEDELICE

(71) Applicant: AGRO SELECTIONS FRUITS, Elne (FR)

(72) Inventors: Arsene Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 138 days.

(21) Appl. No.: 13/815,929

(22) Filed: Mar. 18, 2013

(65) Prior Publication Data

US 2013/0263337 P1 Oct. 3, 2013

(30) Foreign Application Priority Data

Apr. 2, 2012 (EP) ..... 2012/0745

(51) Int. Cl.
*A01H 5/08* (2006.01)

(52) U.S. Cl.
USPC ..... Plt./188
CPC ..... *A01H 5/0856* (2013.01)

(58) Field of Classification Search
USPC ..... Plt./188
CPC ..... A01H 5/0856; A01H 5/0837; A01H 5/08; A01H 5/00
See application file for complete search history.

(56) References Cited

U.S. PATENT DOCUMENTS

PP24,107 P3 * 12/2013 Maillard et al. ..... Plt./188

* cited by examiner

*Primary Examiner* — June Hwu

(74) *Attorney, Agent, or Firm* — Westerman, Hattori, Daniels & Adrian, LLP

(57) ABSTRACT

A new and distinct variety of white flat nectarine tree, denominated 'CAKEDELICE', has flat fruits of very long shelf life without alteration before and after harvesting, and with a semi-sweet white flesh of high eating quality, with a slightly red pigmentation into and around the stone cavity, and an attractive luminous and homogenous purple red skin on a red background.

4 Drawing Sheets

Botanical classification: *Prunus persica* var. *nucipersica*. (L.) Batsch.

Variety denomination: 'CAKEDELICE'.

This application claims priority of Community plant variety right No. 2012/0745 filed on Apr. 2, 2012 (Apr. 2, 2012), which is hereby incorporated by reference in its entirety.

BACKGROUND OF THE NEW VARIETY

The present invention relates to a new and distinct variety of white flat nectarine tree, *Prunus persica* var *nucipersica* (L.) Batsch, which has been given the variety denomination 'CAKEDELICE'. This new tree produces fruit with a long shelf life without alteration both on the tree after growth completion and after harvesting, very good eating quality, semi-clingstone white flesh fruits for fresh market early in August in the Pyrénées-Orientales department (an administrative district), France. Contrast is made to its parents 'ASFNBF0688' (U.S. Plant Pat. No. 22,492) white flat nectarine variety and 'NECTARMAGIE' (U.S. Plant Pat. No. 17,579) white nectarine tree for reliable description. 'CAKEDELICE' is a promising candidate for commercial success in that it has very attractive fruits with very long shelf life without alteration before after harvesting.

ORIGIN OF THE VARIETY

The 'CAKEDELICE' white flat nectarine tree originated in a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year, and are mostly found in Spring and Autumn. In May and October, very intense precipitations occasionally happen. Summer is dry with a few thunderstorms.

The 'CAKEDELICE' variety resulted from a pollinated cross between the 'NECTARMAGIE' (U.S. Plant Pat. No. 17,579) white nectarine tree, which was used as the seed parent, and the 'ASFNBF0688' (U.S. Plant Pat. No. 22,492) white flat nectarine tree, which was used as the pollen parent.

'CAKEDELICE' was provisionally designated, tested and genetically identified by a genetic profile, under number 03.5E.125NBPL and was registered at the Official Catalogue of the Agriculture Ministry of the French Republic on Nov. 27, 2011 under number 4049391. The 'CAKEDELICE' variety was obtained by hybridizing and propagated by grafting on an 'INRA GF677' (non-patented) rootstock trees. It has been determined to have unique tree and fruit characteristics making it worthy for commercial fresh fruit production.

There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety of white flat nectarine tree blooms at the end of February or in March in the Pyrénées-Orientales department, France. More particularly, it blooms between February 28$^{th}$ and March 17$^{th}$, generally 3 days earlier than 'ASFNBF0688' (U.S. Plant Pat. No. 22,492). However, it was observed that its early date of blooming seems to be highly dependant on climatic conditions.

The first fruit of 'CAKEDELICE' nectarine tree ripens at the end of July or early in August, generally about one month earlier than 'ASFNBF0688' (U.S. Plant Pat. No. 22,492). More particularly, 'CAKEDELICE' variety approximately ripens between July 22$^{nd}$ and August 4$^{th}$. However, it was observed that its early date of maturity seems to be highly dependant on climatic conditions.

DESCRIPTION OF THE DRAWINGS

In the accompanying drawing, which are as nearly true as it is reasonably possible to make in a color illustration of this type.

Figure 1:
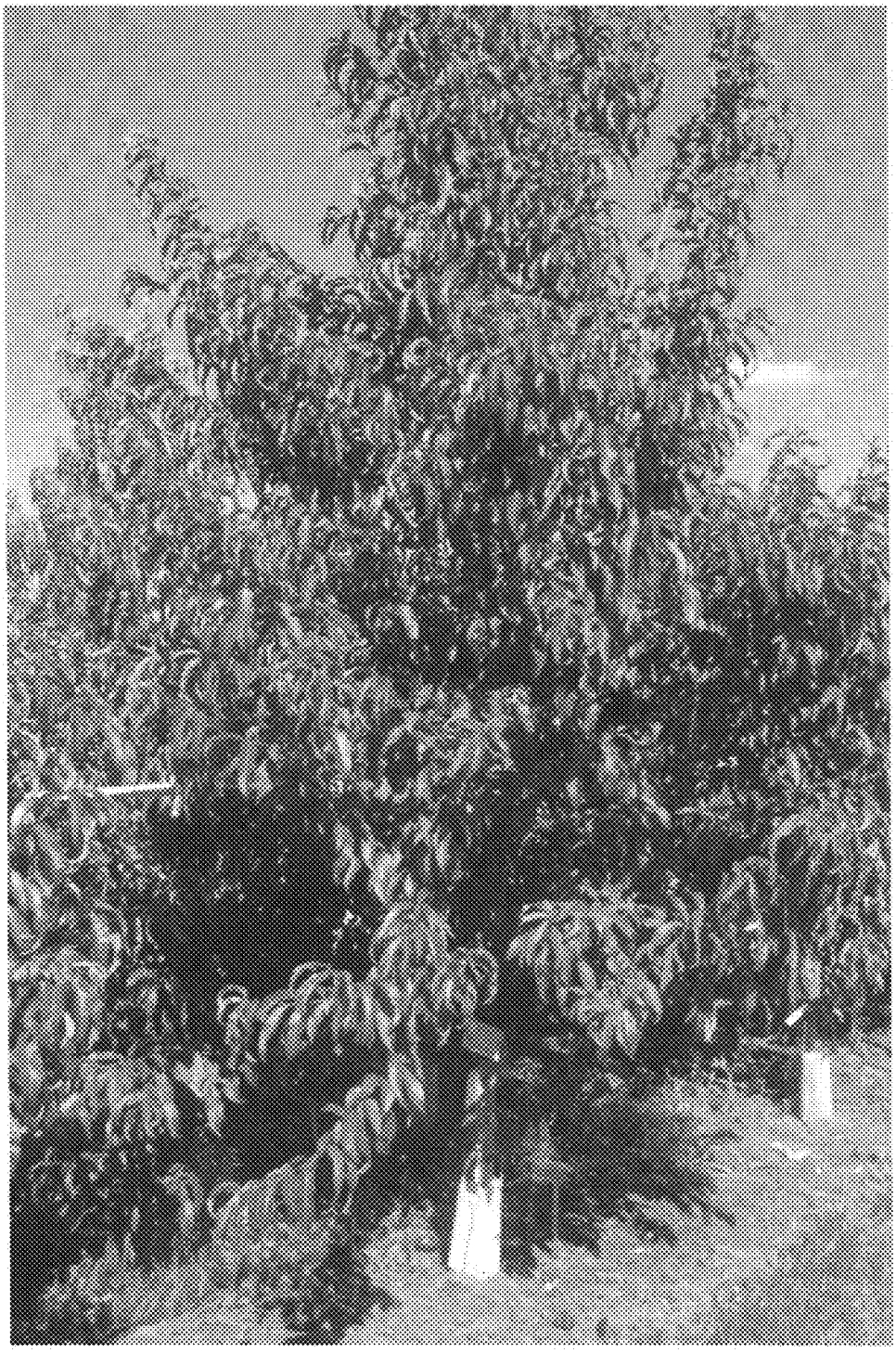
FIG. 1 is a color photograph, which shows a view of a tree of the new variety in its second leaf, in orchard, bearing fruits.
Figure 2:
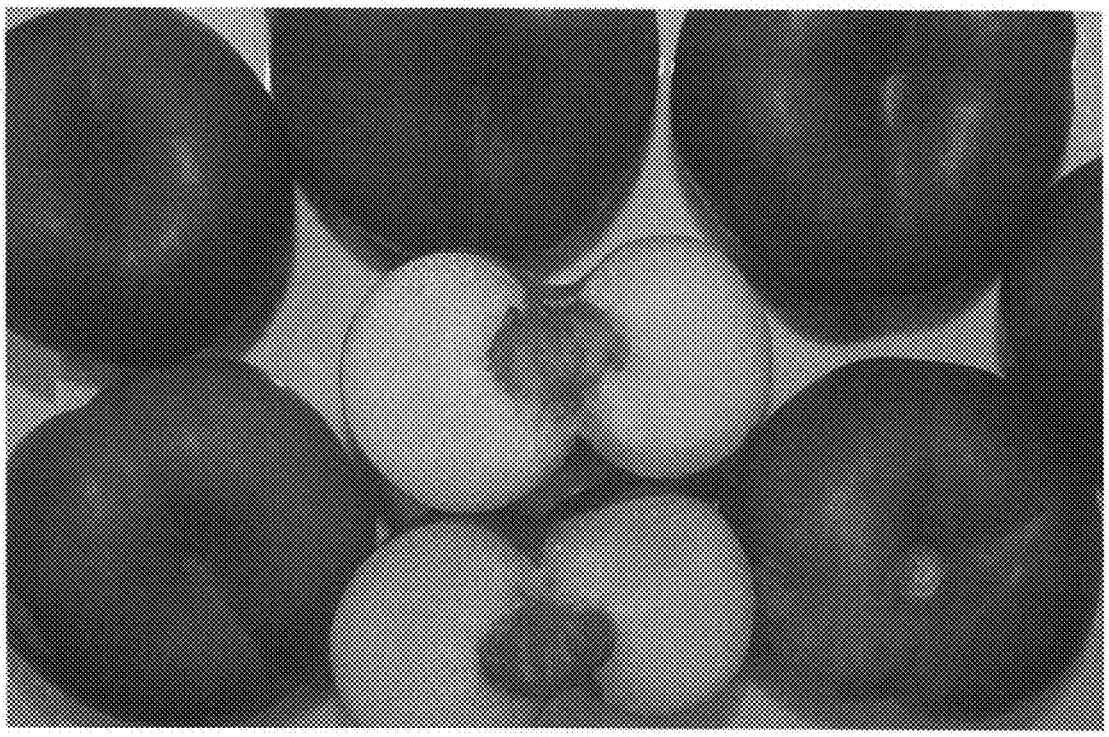
FIG. 2 is a color photograph, which shows typical specimens of the fruits of the new variety, one of the fruits being cut in half with the stone left in one of the halves for depicting the fruit flesh, the stone and the stone cavity of the new variety.
Figure 3:
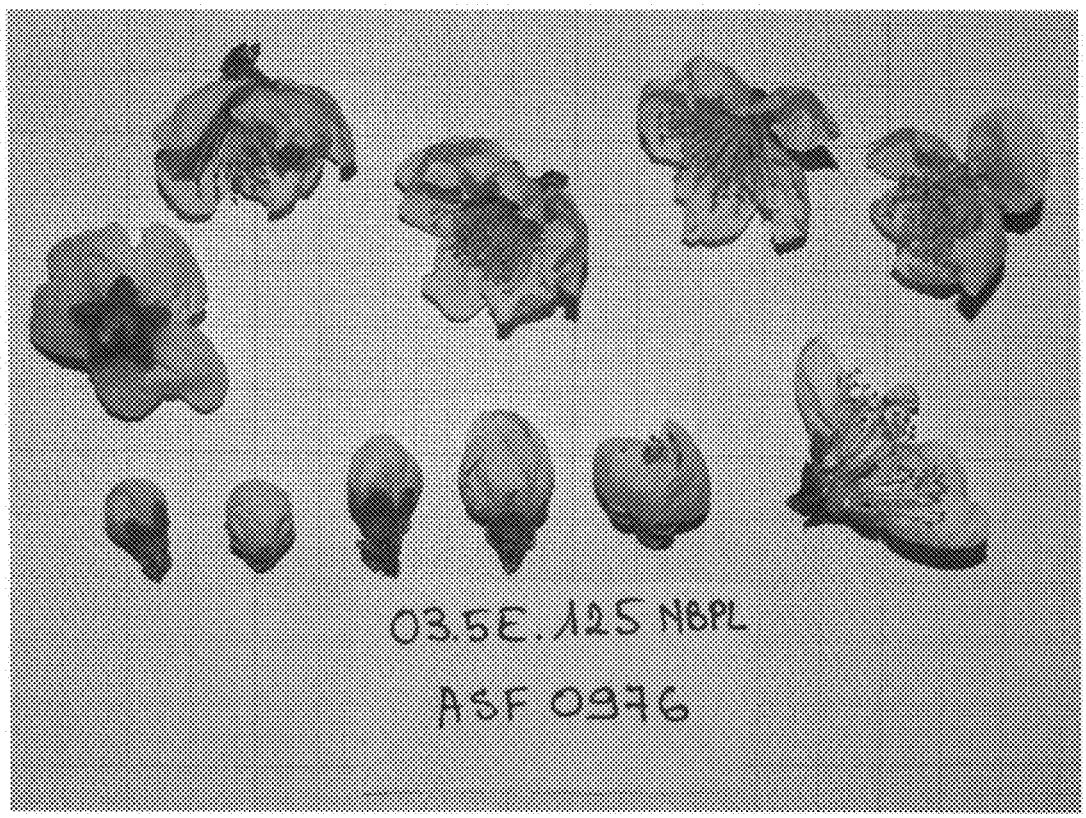
FIG. 3 is a color photograph with reverse and side views of flowers of the new variety, and, with petals removed, reproductive organs of the new variety.
Figure 4:
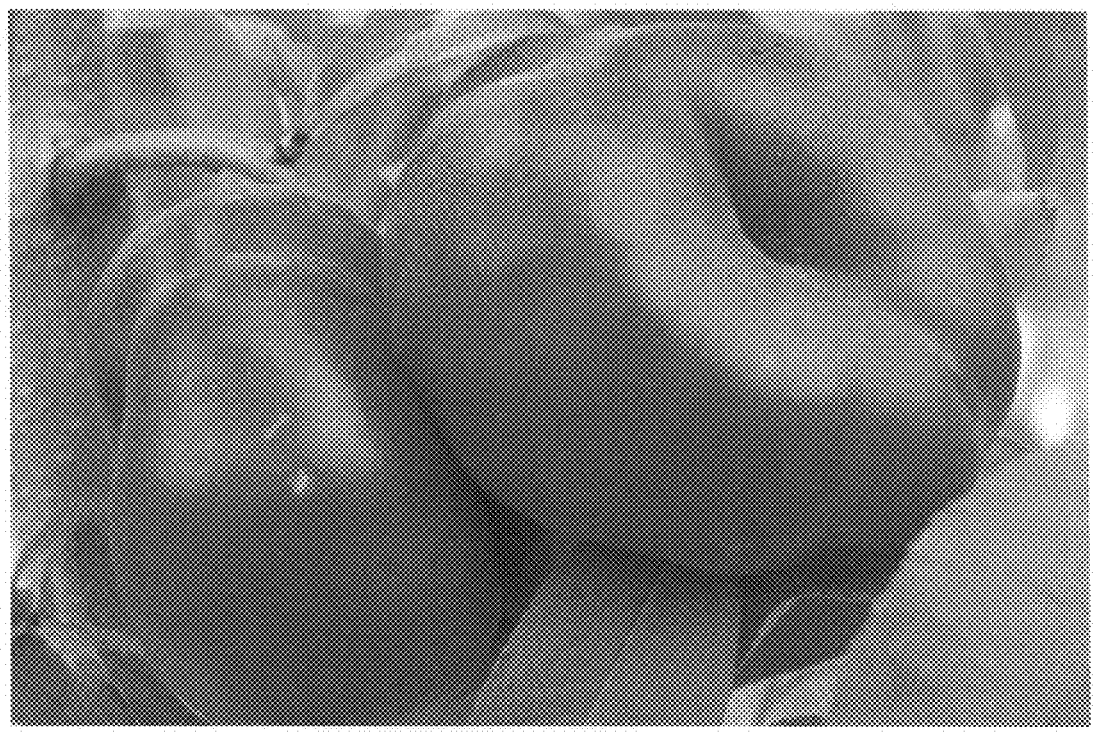
FIG. 4 is a color photograph, which shows a close view of typical fruits of the new variety 'CAKEDELICE' at ripening time.

Due to chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruit by 'CAKEDELICE' is high, due to fruit very long shelf life without alteration after harvesting.

Trees are medium vigorous and large stature half-standing in a semi-flared to semi-upright out aspect. The anthocyanic coloration of flowering shoot is present excluding brushwood side away from sun. The time of beginning of flowering is considered medium; flowering begins at the end of February or during March. The type of flower is showy with medium to large petal size. Petals are medium pink. Leaf glands are present and reniform. The fruit flesh is considered white with a slightly red pigmentation into and around the stone cavity. The fruit skin is thick and colored with a homogenous and luminous purple red blush on a red background. The stone is semi-clingstone, small in size and the flesh is adherent to semi-adherent depending on the fruit maturity. Fruit taste is semi-sweet, very aromatic and with a high level of sugars.

The new variety male parent, which is 'ASFNBF0688' (U.S. Plant Pat. No. 22,492) produces a considerable amount of white flat nectarine tree at the end of August or early in September. In comparison, 'CAKEDELICE' variety ripens approximately one month earlier, at the end of July or early in August as set forth above. Moreover, both varieties produce an important amount of showy flowers and have a very high rate of fruit set. 'CAKEDELICE' fruits have a good and homogenous presentation, round and regular shaped, with a closed pistil cavity, and without any cork formation. Indeed, the cork formation in the pistil cavity of nectarine flat variety is often the cause of conservation problem, therefore rot. Accordingly, a variety without formation/training or presence of cork will generally have better conservation and thus less sensitive to the development of rot. In comparison, 'ASFNBF0688' fruits possess a pistil cavity barely closes, with a little amount of cork, that could lead to a susceptibility to rot. 'CAKEDELICE' fruits are colored with a luminous red on the whole fruit skin compared to 'ASFNBF0688' fruit which are colored in red on a pink cream background.

The new variety female parent, which is 'NECTARMAGIE' (U.S. Plant Pat. No. 17,579), produces white nectarines early in July.

Compared to 'Cakelove' (U.S. Plant Pat. No. 24,107) white flat nectarine tree, 'CAKEDELICE' variety ripens approximately 2 weeks earlier than 'Cakelove', as set forth above. 'CAKEDELICE' fruits show a size bigger than 'Cakelove' fruits.

Pistil cavity of 'CAKEDELICE' varieties are considered more closed than the 'Cakelove' pistil cavity.

DETAILED DESCRIPTION

Referring more specifically to the pomological details of this new and distinct variety of white flat nectarine tree, the following was observed on trees in their fourth growing season (third year of production) under the ecological conditions prevailing at the orchards located near the town of Elne, Pyrénées-Orientales department, France. All observations have been done on rootstock cultivars. Used rootstocks were 'INRA GF677' (non-patented) trees. All major color code designations are by reference to The R.H.S. Colour Chart 2001 (Fourth Edition) provided by The Royal Horticultural Society of Great Britain.

Tree:

*Size*.—Generally. — Considered large. The tree size the first year was approximately 250 cm. The tree was pruned during each following dormant season to a height of approximately 250 cm. Current season shoots growth could reach 60 to 80 cm. The tree size from the second year (second and next years) reached a final height of 310 to 330 cm with current season shoots length comprised. The tree size is consistently reduces to 250 cm the next years.

*Spread*.—Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

*Vigor*.—Considered medium vigorous.

*Productivity*.—Very Productive. Fruit set is spaced by thinning to develop the remaining fruit into the desired market sized fruit. The number of the fruit set varies with the prevailing climatic conditions and cultural practices employed during the bloom period, and is therefore not distinctive of the present variety. A reduce vegetation, obtained with pruning or green pruning, approximately 1 month or 1 month ½ before harvesting flat fruits, significantly promotes fruit qualities, especially growth, color and firmness. Moreover, contamination risks due to *Monilia* or rot are significantly reduced. 'CAKEDELICE' variety is not much sensitive to cracking of pistil cavity, to cork formation into peduncle cavity or to *Monilia*.

*Bearer*.—Very regular. Thinning of 1 fruit out of 3 was necessary for the tree valorisation. Thinning was necessary every year during the years of observation.

*Form*.—The 'CAKEDELICE' variety has a naturally semi-spread to semi-upright shape.

*Density*.—Considered dense.

*Hardiness*.—The present tree was grown and evaluated in France. The variety appears to be hardy under the central Pyrénées-Orientales department typical climatic conditions. Experimentations on different sites with winter chilling requirement comprised between 350 hours and 1200 hours showed a good behaviour of the tree in all cases. Traditionally, flat fruits are more sensitive to critical low temperatures and to climatic variations, because of the flower morphology in which the ovule is less protected than in the classical round fruits. Thus, areas not much exposed to frost are recommended for peach trees growth. However 'CAKEDELICE' trees seem to be very resistant to critical frosty weather.

Trunk:

*Diameter*.—Approximately between 80 and 85 millimeters in diameter when measured at a distance of approximately 30 cm above the soil level.

*Bark texture*.—Considered slightly rough, with lenticels.

*Lenticels*.—Numerous lenticels are present, generally between 2 and 3 lenticels per $cm^2$. The lenticels range in size from approximately 5.0 millimeters to 8.0 millimeters in width, and from 1.5 to 2.5 millimeters in height.

*Lenticel color*.—The outside of lenticels has a silver-grey color (RHS Grey 201 D), whereas the inside is considered brown (RHS Greyed Orange 164 A to RHS Greyed Orange 165 B).

*Bark coloration*.—The bark has a silver-grey color (RHS Brown 200 C or RHS Grey 201 C), slightly deeper than lenticel color.

Branches:

*Size*.—Mature branches and current season shoots are considered medium for the variety.

*Diameter*.—Average as compared to other nectarine varieties. The current season shoots have a diameter from 4.0 to 7.0 millimeters, and mature branches have a diameter from 32.0 to 42.0 millimeters.

*Surface texture*.—Average, wood which is several years old has no furrowed appearance.

*Crotch angles*.—Primary branches are considered variable, but the crotch angles are generally between 60 degrees and 80 degrees from the horizontal axis. This particular characteristic is not considered distinctive of the variety, however.

*Current season shoots*.—Internode length: Generally 25.0 to 35.0 millimeters. Color of mature branches: Considered grey brown (RHS Grey Brown 199 A or RHS Grey Brown N 199 A).

*Current seasons shoots*.—Color. — The color of new shoot tips is considered a pale green (RHS Green 144 A to B) on lower part of new shoot tips, whereas the upper part is colored with a more or less deep brown purple (RHS Greyed Red 183 A), depending both on the position on shoots and the sunlight exposure.

Leaves:

*Size*.—Considered medium for the species. The ratio leaf length/leaf width is 3.58.

*Leaf length*.—Approximately 132.0 to 172.0 millimeters with leaf petiole. The medium length is 154.0 millimeters.

*Leaf width*.—Approximately 35.0 to 49.0 millimeters. The medium width is 43.0 millimeters.

*Leaf base shape*.—Cuneate.

*Leaf form*.—Lanceolate.

*Leaf tip form*.—Short, pointed and acuminate.

*Leaf color*.—Upper leaf surface. — Dark Green (RHS Green 139 A or RHS Yellow Green 147 A). Lower surface. — A lighter green (RHS Green 137 B to C) than the upper leaf surface color.

*Leaf texture*.—Smooth and glabrous, this leaf texture refers to the upper and lower surfaces of the leaf.

*Leaf venation*.—Pinnately veined.

*Mid-vein*.—Color. — Light green, almost cream white (RHS Yellow Green 145 D).

*Leaf margins*.—Slightly undulating.

*Form of leaf margins*.—Considered slightly dentate.

*Uniformity*.—Leaves are isolated or grouped by 2 or 3. In this last case, one leaf of normal size is found with one or two smaller leaves (at least 50% smaller).

*Leaf petioles*.—Size. — Considered medium. Length. — Between 10.0 and 15.0 millimeters. Diameter. — Between 2.0 to 2.5 millimeters.

*Petioles color*.—Upper petiole surface. — Light green, almost yellow (RHS Yellow Green 144 A). Lower surface. — Light green, almost yellow (RHS Yellow Green 144 C to D or RHS Yellow Green 145 B). The color of the lower petiole is a lighter green than the color of the upper surface petiole.

*Leaf glands*.—Size. — Considered medium to large. Their length is about 2.0 millimeters and their width is about 1.0 millimeter. Number. — Generally 2 glands per leaf. Type. — Reniform. Margins. — Smooth and regular. Color. — On young leaves, leaf glands color is considered a light green (RHS Yellow Green 145 B). On older leaves, leaf glands color turns to a dark brown (RHS Grey Brown 199 A to 199 B).

*Leaf stipules*.—Generally. — No leaf stipules were observed. But as seen in the characteristic relative to the leaves uniformity, it is possible to find leaves by groups of 2 or 3, with a normal-size leaf and smaller ones.

*Leaf bud burst*.—Medium.

Flowers:

*Flower buds*.—Generally. — At pre-floral stage of development, the floral buds are conic in form with a round tip. Their form is evolving until blooming, with variables dimensions. Just before blooming, floral buds are approximately 12.0 millimeters wide and approximately 20.0 millimeters long. Color. — This characteristic is dependent upon the proximity to bloom. At pre-floral stage of development, the bottom of the flowers buds, formed by the sepals, is of purple-brown color (RHS Greyed Purple 183 A to C). The corolla, formed by the petals, is generally of pink color (RHS Red Purple 65 C) or deep pink color (RHS Red Purple 73 B to C). Petals color shows an evolution until the end of blooming.

*Hardiness*.—The buds are considered hardy under typical central Pyrénées-Orientales department climatic conditions. No winter injury was noted during the last several years of evaluation in the central Pyrénées-Orientales department, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom*.—Generally at the end of February or during March. The first bloom was observed on Mar. 5, 2009.

*Blooming time*.—Considered medium-season in relative comparison to other commercial nectarine cultivars grown in the Pyrénées-Orientales department, France. The date of full bloom is observed on March, $10^{th}$ at the middle of the blooming period. The date of bloom varies slightly with climatic conditions and cultural practices. Thus the first full bloom was observed from Mar. 5 until Mar. 14, 2009. Last observed blooming times were from Mar. 17 until Mar. 24, 2010, then from Feb. 28 to Mar. 8, 2011, and from Mar. 11 until Mar. 19, 2012.

*Duration of bloom*.—Between 8 and 10 days. This characteristic varies slightly with the prevailing climatic conditions.

*Flower type*.—The variety is considered to have a showy type flower.

*Flower size*.—Considered medium to large. Flower diameter at full bloom is approximately 30.0 to 35.0 millimeters.

*Bloom quantity*.—Considered abundant, approximately 40 flowers per meter, with a good distribution and a high rate of fruit set.

*Flower bud frequency*.—Generally 2 flower buds appear per node, occasionally 1.

*Petal size*.—Generally. — Considered medium to large for the species.

*Length*.—Generally about 20.0 millimeters.

*Width*.—Generally about 19.0 millimeters.

*Petal form*.—Round-shaped.

*Petal count*.—Generally 5.

*Petal texture*.—Smooth, soft and glabrous.

*Petal color*.—Both surfaces of the petal are colored with a medium Pink (RHS Red Purple 65 A to C) and becoming slightly darker until the end of flowering.

*Fragrance*.—Sweet.

*Petal claw*.—Form. — The claw is considered to have a conic form with a slightly rounded tip. Length. — Approximately 5.5 millimeters. Width. — Approximately 4.0 millimeters.

*Petal margins*.—Slightly undulating, sometimes wrinkled.

*Petal apex*.—Generally. — The petal apices are generally wide dome-shaped.

*Flower pedicel*.—Length. — Considered medium to long and having an average length of approximately 4.0 millimeters. Diameter. — Considered average, approximately 2.0 millimeters. Color. — A light brown (RHS Grey Brown N199 C to D).

*Calyx*.—Internal surface texture. — Smooth and glabrous. Color. — The inner surface of the calyx is green yellow (RHS Yellow Group 13 A to B or RHS Yellow Green 150 A to B). The outer surface of the calyx is considered of Purple-brown (RHS Greyed Purple 183 B to D) color.

*Sepals*.—Number. — Generally five sepals. Surface texture. — The outer surface has a short, fine pubescent texture. Size. — Medium. Length. — Approximately 5.0 to 6.0 millimeters. Width. — Approximately 4.0 to 5.0 millimeters. Form. — Ovate. Color. — Both sides of sepals are colored with a purple Brown (RHS Greyed Purple 183 B to D).

*Average number of stamens per flower*.—Approximately 50 stamens per flower.

*Anthers*.—Generally. — Medium in length. Color. — Orange-yellow color (RHS Yellow Orange 16 A to B). The color becomes red to orange red (RHS Greyed Purple Group 178 A) after maturity.

*Pollen production*.—Pollen is abundant, and has a yellow color (RHS Yellow Orange 17 B to C) which may evolve with maturity. The present variety is considered auto-fertile (self-pollinating).

*Filaments*.—Size. — Medium length, between 8.0 and 16.0 millimeters in length. Filaments length is generally equal to the pistil's length, if not slightly longer.

*Color*.—Considered light pink (approximately RHS Red Purple 62 C to D or RHS Red Purple 73 A to B). The color evolves during the blooming.

*Pistil*.—Number. — Usually 1. Generally. — Average in size. Length. — Approximately 14.0 to 16.0 millimeters including the ovary; Generally equal to stamen's length, if not slightly smaller. Color. — Considered a very pale green (RHS Yellow Green 150 D or RHS Yellow Green 151 D). The color evolves during the blooming. Surface texture. — Glabrous.

Fruit:

*Maturity when described*.—Very firm ripe condition (shipping ripe).

*Date of first picking*.—Jul. 22, 2009.

*Date of last picking*.—The date of harvest varies slightly with the prevailing climatic conditions. The 'CAKEDELICE' variety has a grouped maturity. The maturity is grouped within 6 to 9 days and the harvest is generally performed in two runs. Last known picking times were from Jul. 22 to Jul. 31, 2009, then from Aug. 4 to Aug. 11, 2010, then from Jul. 25 to Jul. 31, 2011 and from Jul. 30 to Aug. 7, 2012.

*Size*.—Generally. — Considered medium to large and homogeneous in size.

*Average cheek diameter*.—Approximately 70.0 to 80.0 millimeters.

*Average axial diameter*.—Approximately 46.0 to 50.0 millimeters.

*Typical weight*.—Generally between 145.0 and 180.0 grams. This characteristic is high dependent upon the prevailing cultural practices, and therefore is not particularly distinctive of the variety.

*Fruit form*.—Generally. — Curved and flattened, with few bump. The fruit is generally uniform in symmetry, viewed from the suture's plane.

*Fruit suture*.—Slightly flared and slightly marked, extending from the base to the apex. No apparent callousing or stitching exists along the suture line. Not pointed.

*Suture*.—Color. — The suture has generally a color similar to the whole fruit color. The suture is completely colored with a luminous purple red (RHS Greyed Purple 187 A or RHS Greyed Purple N 186 C).

*Ventral surface*.—Form. — Smooth or very slightly humpy.

*Apex*.—Depressed. Very good closing of pistil cavity.

*Base*.—Semi-flared, shallow.

*Stem cavity*.—Average depth of the stem cavity is about 7.0 to 9.0 millimeters. Average width is about 15.0 millimeters.

*Fruit skin*.—Thickness. — Considered thick and strong, and the adherence of skin to flesh is strong to medium, depending on the maturity stage. Taste. — Semi-sweet, with a high level of sugars. Tendency to crack. — Generally none observed.

*Color*.—Blush color. — This blush color is a luminous and homogenous purple red (RHS Greyed Purple 187 A or RHS Greyed Purple N 186 C). The purple red blush covers 90 to 95% of the fruit skin surface on a red background (RHS Red 53 B). The percentage of the blush on the fruit skin surface can vary, and is generally dependant upon the prevailing conditions under which the fruit was grown. Ground color. — The ground color of the fruit skin surface covers approximately 5% of the fruit skin surface and is considered red (RHS Red 53 B).

*Fruit stem*.—Medium in length, approximately 5.0 to 7.0 millimeters.

*Diameter*.—Approximately 4.0 millimeters.

*Color*.—Pale green (RHS Yellow Green N 145 A to B).

*Flesh*.—Ripens. — The maturing of the flesh is very homogenous and slow. The flesh has a long shelf life. Texture. — Very firm, dense, crunchy, melting, juicy at harvest maturity stage. Fibers. — Not fibrous. Aroma. — Pronounced. Eating quality. — Considered very good and aromatic. Flavor. — Considered semi-sweet and aromatic. The Brix is generally superior to 13 and acidity comprised between 6 and 9 meq/100 ml. Juice. — Very juicy at complete maturity. Brix. — Generally about 15.0 degrees, more particularly between 13.0 and 17.0 degrees. This characteristic varies slightly with the number of fruits per tree, prevailing cultural practices and the surrounding climatic conditions. The Brix can reach much more important values in production areas very sunny and warm, for example in Spain. Flesh color. — Greenish white or white flesh (RHS Green White 157 D or RHS White 155 C) with a slightly red pigmentation (RHS Red 53 A) both into the stone cavity and around the stone where the pigmentation is star-shaped on 2.0 to 3.0 millimeters.

Stone:

*Type*.—Semi-Clingstone to semi-adherent depending on the fruit maturity.

*Size*.—Considered small for the variety. The stone size varies significantly depending upon the tree vigor, crop load and prevailing growing conditions.

*Length*.—Approximately 22.0 to 25.0 millimeters.

*Width*.—Approximately 21.0 to 23.0 millimeters.

*Diameter*.—Approximately 14.0 to 16.0 millimeters.

*Form*.—Oblate.

*Base*.—Straight.

*Apex*.—Shape. — The stone apex is oblate.

*Stone cavity*.—Considered small in size, with shape and dimensions corresponding to the stone's dimensions.

*Stone surface*.—Surface texture. — The pit is transversely furrowed on its entire surface. Furrows are deeper and more oblate on lateral sides. Ridges. — The surface texture is generally characterized by more prominent ridges along the ventral edges and at the apical tip.

*Ventral edge*.—Width. — Considered small to medium, and having a dimension of approximately 3.0 millimeters at mid-suture.

*Dorsal edge*.—Shape. — Grooved.

*Stone color*.—The color of the dry stone is generally considered orange brown (RHS Greyed Orange N 170 B or RHS Greyed Orange 174 B to C).

*Tendency to split*.—Splitting is absent or very low, depending on climatic conditions between blooming period and stone hardening.

*Kernel*.—Size. — The kernel size is considered small or medium. Length. — Approximately 10.0 millimeters. Width. — Approximately 8.0 millimeters. Thickness. — Approximately 6.0 millimeters. Form. — Considered elliptic and oblate, sometimes double. Pellicle. — Pubescent. Color. — The kernel skin is light orange yellow (RHS Greyed Orange 164 A or RHS Greyed Orange N 167 A). The almond, which is the seed of the kernel, is cream-white (RHS White 155 B) with a bitter tasting. The kernel and its embryo are mature at the time of fruit maturity.

Use: The subject variety 'CAKEDELICE' is considered to be a white flat nectarine tree with a mid-season maturity, and which produces fruits that are considered firm, attractively and luminously colored. Fruits have a semi-sweet taste and are excellent for uncooked consumption, crunchy or melting and juicy when at full maturity. Fruits have excellent gustative qualities. In particular, 'CAKEDELICE' fruits are very easy to eat, with their doughnut shape. Moreover, the non pointed stone shape is reassuring, especially for parents, and thus, there is no need to cut the fruit before eating. Due to their flesh quality, firmness and density, they can also be commercialized as $4^{th}$ range product (packed fruit or fruit in bags for example). And they are also useful for both local and very long distance shipping.

Keeping quality: Remarkable. Fruits have a slow maturation and a long shelf life both on the tree after growth completion and after harvesting without alteration. After growth completion fruits are preserved more than one week on the tree. After harvest, fruits are well preserved more than 4 weeks at 2.0 degree Celsius.

Shipping quality: Considered very good. The fruit of the new white flat nectarine variety showed minimal bruising of the flesh or skin damage after being subjected to normal harvesting and packing procedures. Its resistance to handling during harvest and packing and its long shelf life without alteration after harvest easily permit at least 4 weeks-shipping at 2 degrees Celsius.

Resistance to disease: No particular susceptibilities were noted. The present variety is not very sensitive to powdery mildew and *Monilia*, or conservation diseases and decay due to its thick and strong skin.

Although the new variety of white flat nectarine tree possesses the described characteristics when grown under the ecological conditions prevailing near Elne, Pyrénées-Orientales department, France, it should be understood that variations of the usual magnitude and characteristics incident to changes in growing conditions, fertilization, pruning, pest control and horticultural management are to be expected.

We claim:

1. A new and distinct variety of white flat nectarine tree as illustrated and described, characterized by flat fruits of very long shelf life without alteration before and after harvesting, and with a semi-sweet white flesh of high eating quality, with a slightly red pigmentation, and an attractive luminous and homogenous purple red skin on a red background.

* * * * *